(12) United States Patent
Magavi et al.

(10) Patent No.: US 8,967,024 B2
(45) Date of Patent: Mar. 3, 2015

(54) DEVICE TO COLLECT AND SEGREGATE TISSUE SAMPLES SECTIONED ON A MICROTOME

(75) Inventors: Sanjay Shivayogi Magavi, Cambridge, MA (US); Jack Barger, Poway, CA (US); Michael Paul Emery, Santee, CA (US); James Edward Sinclair, Carlsbad, CA (US); Jorge Arturo Ayala, San Diego, CA (US)

(73) Assignee: Vertex Pharmaceuticals, Inc., Cambridge, MA (US)

( * ) Notice: Subject to any disclaimer, the term of this patent is extended or adjusted under 35 U.S.C. 154(b) by 496 days.

(21) Appl. No.: 13/187,416

(22) Filed: Jul. 20, 2011

(65) Prior Publication Data

US 2013/0019725 A1   Jan. 24, 2013

(51) Int. Cl.
*G01N 1/06* (2006.01)
*B26D 7/18* (2006.01)
*B26D 7/32* (2006.01)

(52) U.S. Cl.
USPC ..... 83/98; 83/149; 83/165; 83/167; 83/915.5; 422/536

(58) Field of Classification Search
USPC ........... 83/23, 24, 78, 98, 109, 149, 162, 165, 83/167, 915.5; 422/509, 513, 536
See application file for complete search history.

(56) References Cited

U.S. PATENT DOCUMENTS

| | | | | |
|---|---|---|---|---|
| 3,462,969 A * | 8/1969 | Grasenick et al. | | 62/373 |
| 3,680,420 A * | 8/1972 | Blum | | 83/167 |
| 5,713,255 A * | 2/1998 | Izvozichikov et al. | | 83/24 |
| 5,974,811 A * | 11/1999 | Heid et al. | | 62/78 |
| 7,146,895 B2 * | 12/2006 | Kong et al. | | 83/705 |
| 2009/0181457 A1 | 7/2009 | Schmitt | | |
| 2010/0000383 A1 | 1/2010 | Koos et al. | | |
| 2010/0184127 A1 * | 7/2010 | Williamson et al. | | 435/40.52 |
| 2013/0078670 A1 * | 3/2013 | Williamson et al. | | 435/40.52 |

FOREIGN PATENT DOCUMENTS

JP   2007033312   2/2007

OTHER PUBLICATIONS

International Search Report and Written Opinion in PCT Application No. PCT/US2012/046911, filed Jul. 16, 2012, dated: Sep. 21, 2012.

* cited by examiner

*Primary Examiner* — Clark F. Dexter
(74) *Attorney, Agent, or Firm* — Knobbe Martens Olson & Bear LLP

(57) ABSTRACT

Apparatuses and methods for handling a portion of a tissue sample when sectioned by a microtome. The apparatuses include a container, a tissue sample holder in the container, and one or more outlets configured to allow flow of a fluid from the container. The flow through the outlet causes a portion of the tissue sample sectioned by a microtome to move into the outlet. The methods include sectioning one or more portions of a tissue sample, and flowing a fluid past the tissue sample to cause the one or more portions of the tissue sample to move away from the tissue sample and toward at least one fluid outlet.

12 Claims, 7 Drawing Sheets

DEVICE TO COLLECT AND SEGREGATE TISSUE SAMPLES SECTIONED ON A MICROTOME

BACKGROUND OF THE INVENTION

1. Technical Field

The embodiments disclosed herein relate to microtome systems for sectioning tissue samples.

2. Introduction

A microtome apparatus is one example of a sectioning instrument used extensively to cut extremely thin sections of material, including, for example, plant tissue, animal tissue, or other types of tissue samples. Conventional microtomes, such as microtome 50 shown in FIG. 1, include a blade 51 that can be extended to cut off a single, thin section or portion 71 from the top of a tissue sample 70 supported on a tissue support structure 30 while submerged in a reservoir in a container 20. After sectioning, the portion 71 floats in the reservoir (typically aqueous buffer solution, or the like) within the container 20, and is subsequently manually transferred with a tool such as a swab or tweezers to a container such as a well of a multi-well plate, a Petri dish, a microscope slide, or the like, to allow for further analysis, testing and/or storage of the section.

Conventional microtome processes can be repetitive, tedious and laborious, requiring dedicated laboratory personnel to continuously operate and monitor the apparatus as each section is produced. Further, the tissue samples can become contaminated or damaged during their handling by laboratory personnel, increasing operational costs. Thus, there is a need for an efficient microtome apparatus and process that can provide high quality, sectioned tissue samples with reduced waste and contamination.

SUMMARY OF THE INVENTION

In one embodiment, an apparatus for handling a portion of a tissue sample when sectioned by a microtome is provided. The apparatus includes a container, a tissue sample holder in the container, and one or more outlets configured to allow flow of a fluid from the container. The one or more outlets is positioned proximate to the tissue sample holder such that flow through the outlet causes a portion of the tissue sample sectioned by a microtome to move into the outlet.

In another embodiment, a method of handling one or more portions of a tissue sample sectioned by a microtome is provided. The method comprises the steps of sectioning one or more portions of a tissue sample, and flowing a fluid past the tissue sample to cause the one or more portions of the tissue sample to move away from the tissue sample and toward at least one fluid outlet.

In yet another embodiment, an apparatus for handling one or more portions of a tissue sample sectioned by a microtome is provided. The apparatus includes means for sectioning at least one portion of a tissue sample and means for flowing a fluid past the tissue sample. The means for flowing the fluid past the tissue sample cause the one or more portions of the tissue sample to move away from the tissue sample and toward at least one fluid outlet.

For purposes of summarizing the invention and the advantages achieved over the prior art, certain objects and advantages of the invention have been described above and as further described below. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other aspects of the invention will be readily apparent from the following description and from the appended drawings (not necessarily to scale), which are meant to illustrate and not to limit the invention, and in which.

DETAILED DESCRIPTION

The embodiments disclosed herein relate to apparatus and methods for handling a portion of a tissue sample when sectioned by a microtome.

Embodiments will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments disclosed herein. Furthermore, embodiments disclosed herein may include several novel features, no single one of which is solely responsible for its desirable attributes or which is essential to the embodiments herein described.

Figure 1:
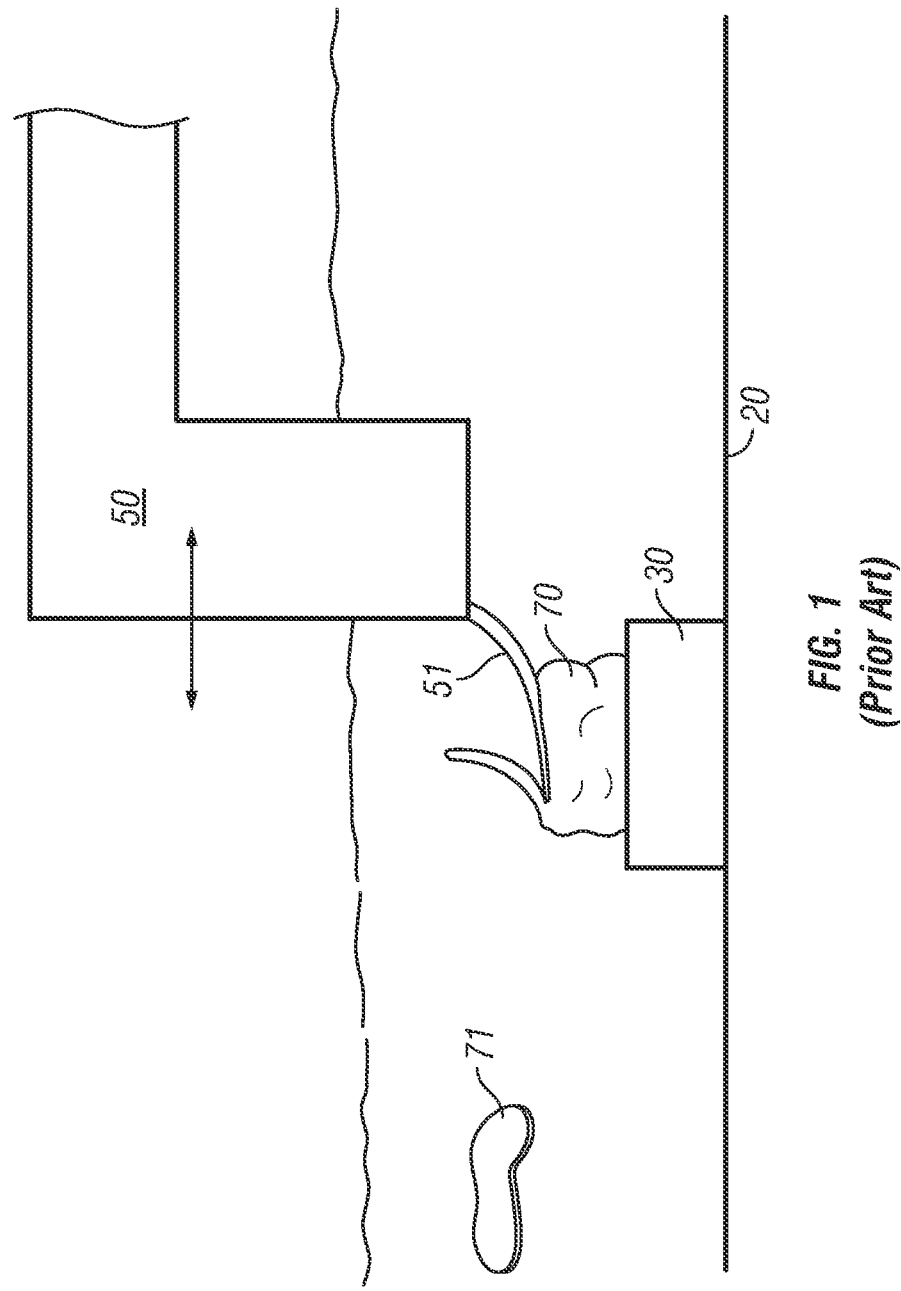
FIG. 1 is a side view of a conventional apparatus for sectioning a portion of a tissue sample.
Figure 2:
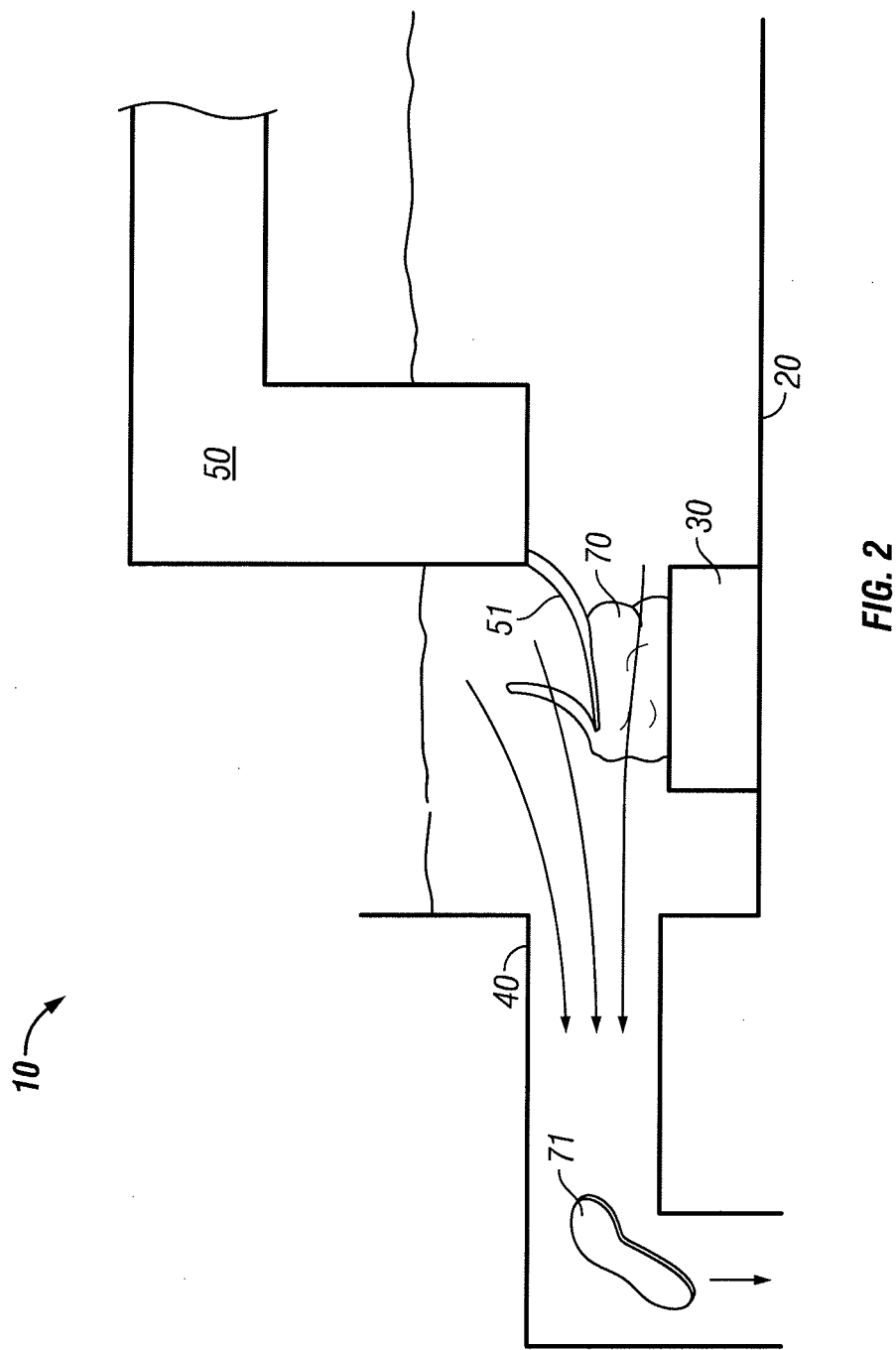
FIG. 2 is a side view of one embodiment of an apparatus for handling a portion of a tissue sample.
Figure 3:
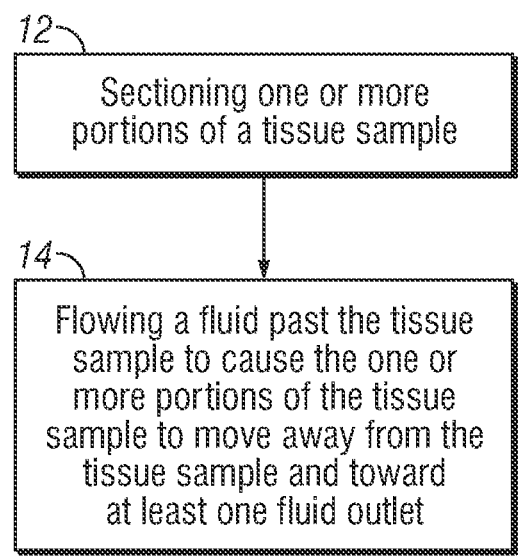
FIG. 3 is a flowchart illustrating a method of handling one or more portions of a tissue sample sectioned by a microtome, according to one embodiment.

FIG. 2 is a side view of one embodiment of an apparatus 10 for handling a portion 71 of a tissue sample 70. FIG. 3 is a flowchart illustrating a method of handling one or more portions of a tissue sample sectioned by a microtome, according to one embodiment. It will be understood that the actions summarized in the flowchart in FIG. 3 are neither exhaustive nor exclusive, and that additional actions may intervene between those disclosed. Furthermore, not all of the disclosed actions must occur. While the following description refers to the apparatus of FIG. 2, it will be appreciated that the method of FIG. 3 can be applied to other apparatuses disclosed herein, as well as to other suitable tissue sample handling apparatuses.

Referring to FIGS. 2-3, one or more portions 71 of tissue sample 70 can be sectioned (block 12 of FIG. 3) from tissue sample 70. Fluid can then be flowed (block 14 of FIG. 3) past the tissue sample 70 to cause the one or more portions 71 of the tissue sample 70 to move away from the tissue sample 70 and toward at least one fluid outlet 40. For example, as described elsewhere herein, fluid can be flowed (in some embodiments, using a laminar or nearly laminar flow) from an inlet to a drain (e.g., FIG. 4) within container 20, to move flow generally towards and past the tissue sample 70. After entering the fluid outlet, the sectioned slice 71 of the tissue sample can be routed along a conduit 41 that forms a fluid channel (e.g., FIG. 4) to a designated container such as a specific well of a multiwell plate, such as a well 91 of a multiwell plate 90 (e.g., FIG. 4). As will be explained further below, as sections of the sample are made, they can sequentially move out the outlet 40 and into the channel formed by conduit 41, under the influence of the flowing fluid, and into successive desired containers. The movement of a set of containers or movement of the end of the channel formed by conduit 41, can also be automated, so that sectioning itself and the transfer/registration of the sectioned samples can occur without manual manipulation of any samples or containers, freeing laboratory personnel of this previous time consuming manual task.

In some embodiments, flowing the fluid, block 14, can comprise increasing flow through the at least one outlet 40 in response to completing a cutting stroke during the sectioning, block 12. Such flow increase can be provided, for example, by moving a valve to an open position at the point when the cutting stroke is completed. The valve can be opened for various lengths of time; in one embodiment, the valve is opened for approximately 400 ms. In some embodiments, one or more sensors (e.g., FIG. 6) can provide feedback as to when the cutting stroke is completed, or near completion, to control the timing of the opening and closing of the valve.

In some embodiments, flowing the fluid, block 14, comprises allowing flow through the one or more outlets 40 at a first flow rate prior to the completing of a cutting stroke, and allowing flow through the one or more outlets 40 at a second larger flow rate subsequent to the completing of a cutting stroke. The first flow rate can be zero, or can be a relatively small bleed flow. The second flow rate can correspond to increasing flow through the one or more outlets 40, for example, by moving a valve to an open position.

In some embodiments, the method of handling one or more portions of a tissue sample sectioned by a microtome can further comprise inhibiting the flow of a fluid through the one or more outlets 40. Inhibiting can comprise restricting the flow by closing a valve in the outlet channel formed by conduit 41.

Sectioning, block 12, can comprise sectioning a plurality of portions 71 of the tissue sample 70 with the microtome 50. Such sectioning of the plurality of portions 71 of the tissue sample 70 can comprise sectioning a first portion and a second portion, either sequentially, or at substantially the same time.

Figure 4:
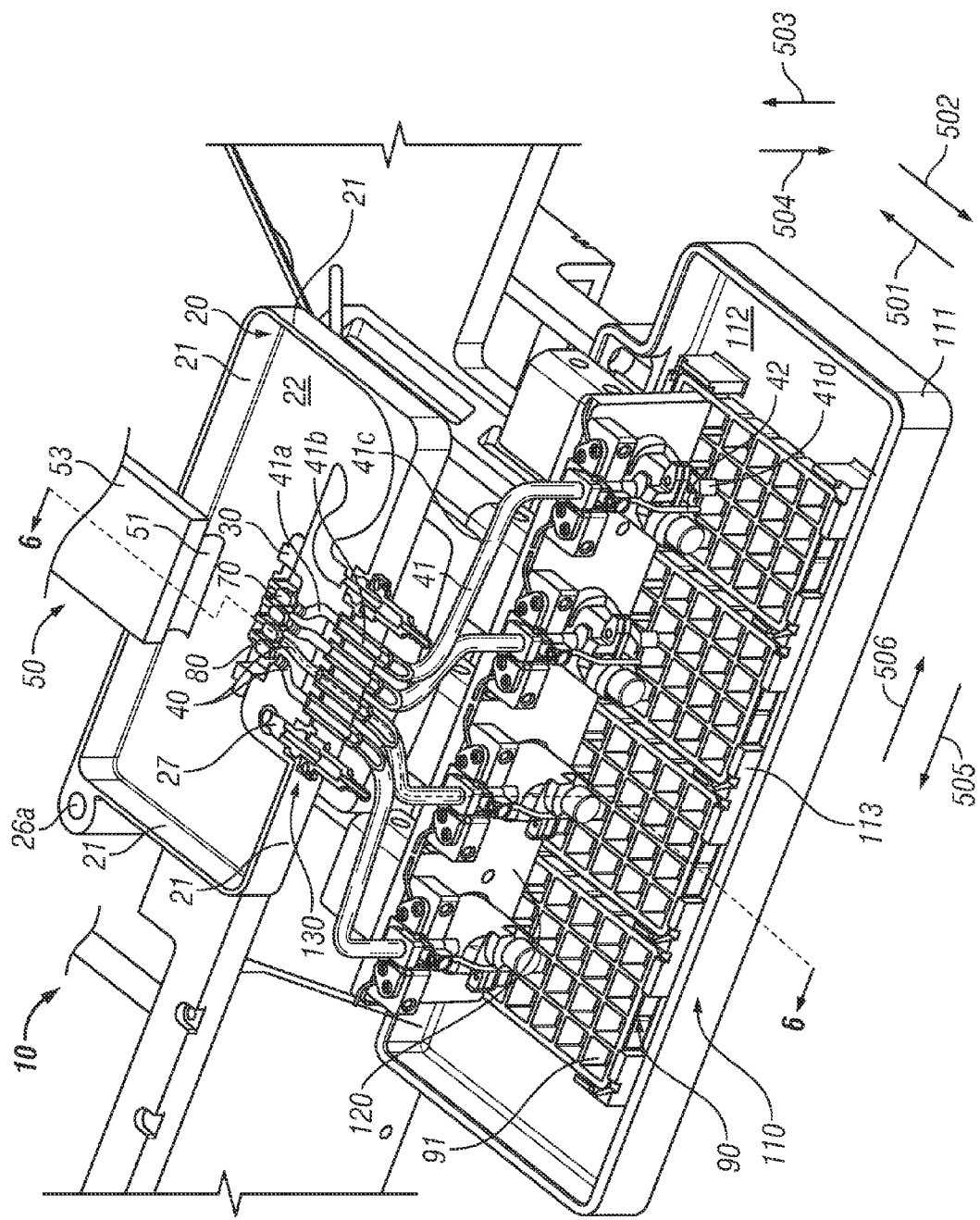
FIG. 4 is a perspective view of one embodiment of an apparatus for handling a portion of a tissue sample, with a portion of the view shown as a cross-section taken along line 4-4 of FIG. 5.

For example, blade 51 of microtome 50 can be positioned with respect to the tissue sample 70 such that the top of tissue sample 70 is slightly above (e.g. 10, 50, 100 micrometers, for example) the cutting plane of blade 51. Blade 51 can advance, (e.g., in the direction shown by directional arrow 502; FIG. 4), to section a first portion 71 from tissue sample 70. Blade 51 can be advanced at a variety of speeds. The blade speed and flow rates during sectioning are preferably selected to facilitate clean cutting of the section and smooth movement of the sample toward the outlet 40 and into the channel formed by conduit 41. Flow rate and blade speed during the cutting process may be selected to cause the portion 71 of tissue sample 70 that is being sectioned to curl upward away from the tissue sample 70 and toward the outlet 40 as the cutting progresses. However, blade speeds and flow rates that are too large can cause the section 71 to fold over onto the front of the tissue sample 70. This is preferably avoided, as it may cause the blade 51 to ride up and over the folded section 71, which can result in an incomplete cut and retention of the section 71 to the front of the tissue sample 70. As mentioned above, shortly after the cut is complete, the flow rate through the outlet 40 may be increased to wash the section 71 into the outlet 40 and out the channel formed by conduit 41. After the first portion is sectioned from sample 70, blade 51 can retract (e.g., in the direction shown by directional arrow 502; FIG. 4).

Tissue sample 70 and blade 50 can then be positioned with respect to each other, by moving sample 70 and/or blade 50 (e.g., in either or both of directions 503 and 504, respectively; FIG. 4), such that a second portion of tissue sample 70 is above the cutting plane of blade 51. The flow rate may then be decreased (or possibly stopped completely), and blade 51 can again be advanced, to section a second portion of tissue sample 70 with blade 51. In this way, a plurality of portions of a tissue sample 70 can be sectioned with microtome 50, wherein the second portion of the sample is sectioned sequentially with respect to the first portion. The aforementioned sequential sectioning operation can be repeated, for example, until the tissue sample 70 is depleted, and/or replaced with another sample. As sections are completed, each one can be routed to a desired container in an automated manner.

In some embodiments, two or more tissue samples 70 can be mounted on tissue sample holder 30. As shown in more detail below, each tissue sample may be associated with its own outlet. Blade 51 of microtome 50 can be positioned with respect to the two or more tissue samples 70 such that a first portion of a first tissue sample 70 and a second portion of a second tissue sample 70 are above the cutting plane of blade 51. Blade 51 can be advanced to section the first and second portions 71 from the first and second tissue samples 70, for example, in a single cutting stroke. In this way, sectioning a plurality of portions 71 of a tissue sample 70 with microtome 50 can comprise sectioning a plurality of portions 71 of a plurality of tissue samples 70 with microtome 50 at substantially the same time. This operation for sectioning a plurality of portions of a plurality of tissue samples 70 can be repeated, for example, using the sequential operation described above, to sequentially section two or more portions of each tissue sample in the plurality of tissue samples.

As used herein, "substantially the same time" means that a single cutting stroke of blade 51 need not necessarily section the two or more tissue samples 70 simultaneously. For example, the edge of blade 51 can comprise an irregular shape, such that a first portion of blade 51 cuts a first tissue sample prior to, but at substantially the same time as, a second portion of blade 51 cutting a second tissue sample, during the same cutting stroke. Additionally, the orientation of the edge of blade 51 and the two or more samples 70 can be substantially parallel or non-parallel with respect to each other, such that a single cutting stroke cuts through two or more tissue samples sequentially.

Figure 5:
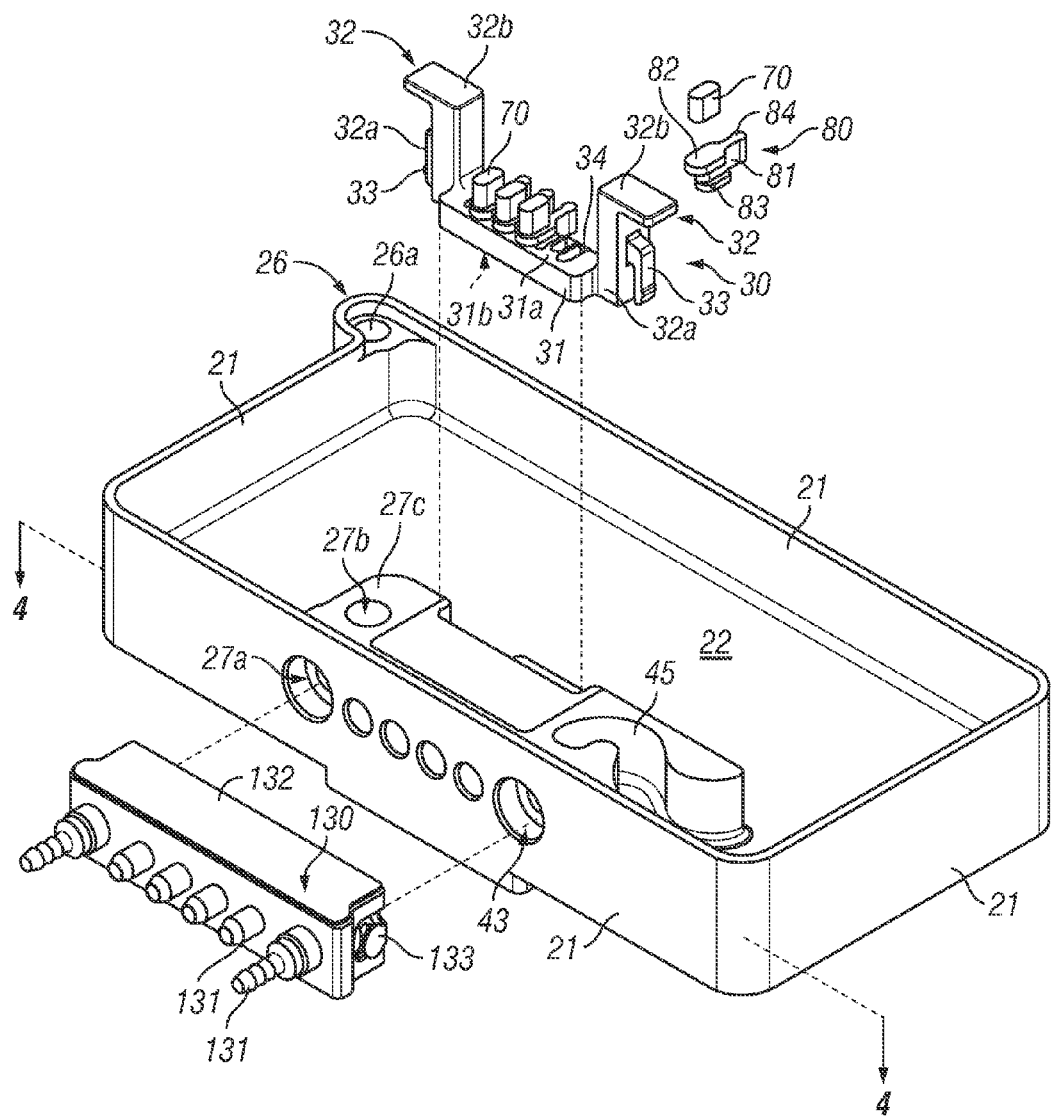
FIG. 5 is a partial exploded perspective view of one embodiment of the apparatus of FIG. 4.
Figure 6:
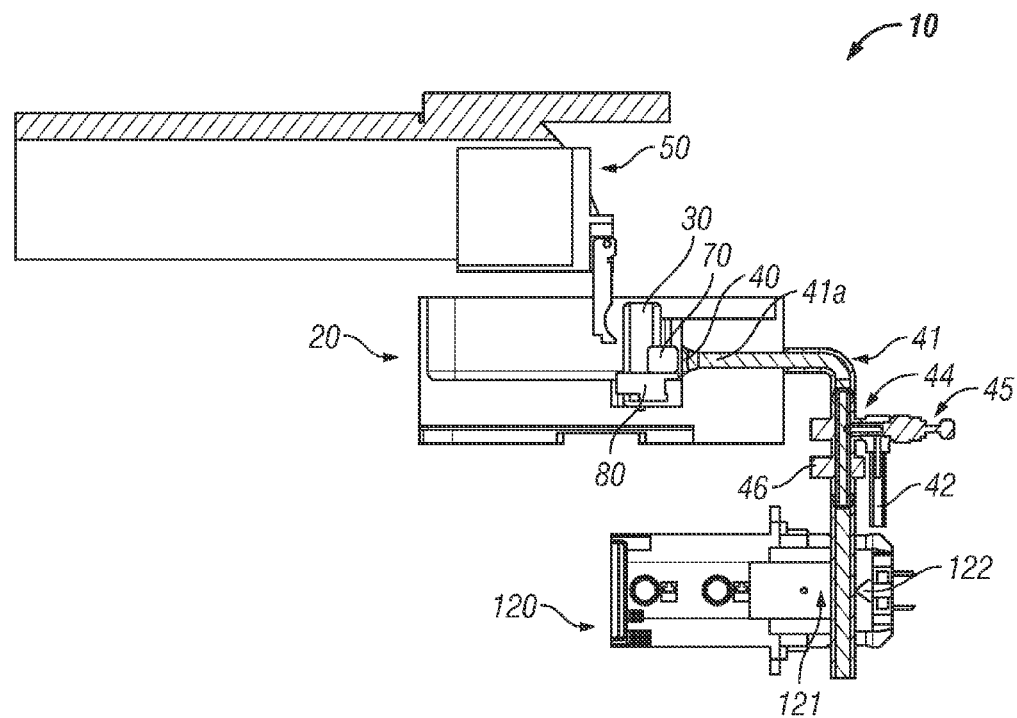
FIG. 6 is a side cross-sectional view of one embodiment of an apparatus for handling a portion of a tissue sample taken along line 6-6 of FIG. 4.

FIGS. 4-6 illustrate various views of one embodiment of one specific apparatus 10 for handling a portion 71 (e.g., a sectioned layer or slice) of one or more tissue samples 70 when a sample 70 is sectioned by the microtome 50 that has been fabricated by the applicants. Apparatus 10 can include the container 20, and the tissue sample holder 30 configured to support the one or more tissue samples 70. FIG. 4 shows a cutaway view of the front of the tray of FIG. 5 to illustrate the outlets 40 and the coupling between the outlets and the channels that route the tissue sections to their desired containers.

Apparatus 10 can include one or more outlets 40 configured to allow flow of a fluid from the container 20. The outlets 40 can be positioned proximate to the tissue sample holder 30 such that flow through the outlet 40 causes a portion 71 of the tissue sample 70 sectioned by the microtome 50 to move into the outlet 40. One or more conduits (e.g., conduits 41, 42; FIG. 4) may be configured to be in fluid communication with outlet 40, as described further herein. In some embodiments, apparatus 10 can include one or more storage plates 90 (FIGS. 4 and 7) configured to receive and store the sectioned portion 71 of the tissue sample 70. In some embodiments, apparatus 10 can include a tray (e.g., a movable tray) 110 (FIG. 4) that can support the storage plate 90.

Microtome 50 can comprise any of a number of different microtome devices known or described herein. Microtome 50, and many of the components of apparatus 10 described herein, can be manually and/or automatically operated, such as with a control system and/or other automation components. Apparatus 10 can include one or more movable elements that comprise any of a number of devices that can facilitate linear and/or rotational motion between two components. Additionally or alternatively, many of the fluid control components described herein, such as the valves, drains, flow controllers, etc., can be automatically or manually controlled.

Microtome 50 can comprise a sectioning element (e.g., a knife or blade) 51 attached to an arm or other blade support structure 53 that can advance (e.g., directional arrow 502) and retract (e.g., directional arrow 501) with respect to one or more tissue samples 70, such that blade 51 can section a portion 71 of tissue sample 70. In some embodiments, the blade 51 and the one or more tissue samples 70 can move with respect to each other (e.g., directional arrows 503; 504, or approximately vertically), to allow two or more portions 71 to be sequentially sectioned from a tissue sample 70, or to adjust the thickness of the portion 71 of the tissue sample 70 that is sectioned. For example, blade 51 can be held stationary, and tissue sample 70 can be moved slightly upwardly (e.g., approximately 50 μm), to section a portion 71 from sample 70.

In some embodiments, blade 51 can move laterally with respect to tissue sample 70 (e.g., directional arrows 505-506), for example, to select the portion of the blade 51 that sections one or more tissue samples 70 during the cutting stroke. Any of the relative movements (e.g., in any of directions 501-506) between blade 51 and one or more tissue samples 70 can be provided by attaching one or more of the aforementioned movable elements to blade 51 and tissue samples 70, or an intermediary structure, such as tissue sample holder 30, container 20, arm 53, or other intermediary structure. In a preferred embodiment, microtome 50 is a vibrating microtome, and thus is configured to vibrate blade 51 during the sectioning of tissue samples 70, to provide a cleaner and more accurate cut.

Referring to FIG. 4, apparatus 10 can include a controller or processor element that can be implemented to automate and/or control various aspects of the apparatus 10 and methods of using apparatus 10 described herein. It will be appreciated that the processor element of the apparatus 10 may be integral to the housing of the apparatus 10, or all or part of the processing and control circuits can be separate from the apparatus 10 itself. In some embodiments, the processor can be a specialized microcontroller which is designed specifically for controlling the elements of the apparatus 10. Alternatively, the processor can be a standard personal computer device such as an Intel processor-based PC running an off the shelf operating system such as Windows, Linux, MacOS, or the like. As used herein, the term "processor" generally refers to one or more logic and control circuits which are connected to the apparatus 10 to control the operation of various components of the apparatus as described herein. In some embodiments, the processor can include direct hardware interface such as a USB port, an RS232 interface, and IP network interface (wired or wireless), or some other type of connection, to load software to control the components and functions of the apparatus 10. In some embodiments, the processor is integrated into the apparatus, which then interfaces with a touch-screen user interface that enables the user to set the parameters for automated control of the different components of the apparatus.

In some embodiments, the processor can include software that allows the user to enter the timing and parameters for controlling one or more components of the apparatus 10, such as the movement of microtome 50, container 20, storage plate 90, and/or tray 110 with respect to each other, and the control of the flow of fluid within and/or through any of these components. In some embodiments, the software allows the user to program the apparatus to complete a procedure for sectioning one or more tissue sample(s), including a first sectioning step (e.g., the movement of the microtome blade to section a tissue sample), the flow of fluid and movement of the sectioned tissue sample into the outlet, the movement of the sectioned tissue sample into a storage tray, and the indexing of the storage tray prior to repeating these steps on a second tissue sample section. In some embodiments, the processor can allow for automated collection of "run data" including, for example, temperature, pressure, flow and volume measurements, count of sectioned tissue samples, operator identity, date and time, etc.

Continuing to refer to FIGS. 4-6, tissue sample holder 30 can comprise any of a number of shapes and materials capable of supporting one or more tissue samples 70 within container 20 in a position to facilitate the sectioning of samples 70 by a microtome. Tissue sample holder 30 can be a rigid or semi-rigid material, such as metal, glass, ceramic, or plastic, and can be a flexible or semi-flexible material, such as plastic. Tissue sample holder 30 and its components generally comprise a material with sufficient rigidity and strength to support tissue sample 70 when being sectioned by microtome 50. Tissue sample holder 30 can also comprise a shape and material that is reasonably smooth and free from burrs or sharp edges, to facilitate low turbulence fluid flow on and around its surfaces, and to prevent snagging or catching of objects on its surface. Tissue sample holder 30 preferably comprises a hydrophobic material, and more preferably, a material suitable for use within a clinical environment for handling tissue samples. Tissue sample holder 30 can comprise any combination of, and/or can be coated with, one or more of the aforementioned materials.

Tissue sample holder 30 can be attached (e.g., permanently or removably) to a portion of container 20, or an intervening structure. Tissue sample holder 30 can comprise a separate component, or can be formed integrally with container 20. For example, tissue sample holder 30 can comprise a portion of a surface of base 22 of container 20, or a surface of a structure protruding from base 22, on which tissue sample 70 can be positioned and sectioned by microtome 50. It will be understood that tissue sample holder 30 can be configured to support any of a number of different quantities of tissue samples 70, and is shown supporting four tissue samples 70 for illustrative purposes only. Moreover, the tissue samples 70 are shown in a single row, to be sectioned by a single microtome blade 51 for illustrative purposes only. Embodiments of apparatus 10 can include additional rows and/or columns of tissue samples, to form various 2 or 3-dimensional arrays or matrices of tissue samples, to be sectioned by two or more microtome blades at various orientations, either simultaneously or sequentially.

Tissue sample holder 30 can comprise a tissue sample holder base 31 configured to support one or more tissue samples 70. Base 31 can be any of a number of shapes, such as an elliptical, rectangular, trapezoidal, or other regular or irregular shape. Base 31 can include an upper surface 31a which can face towards and support tissue sample 70, and a lower surface 31b, which can face towards and be supported by container 20 (e.g., base 22 of container 20) when tissue sample holder 30 is attached to container 20 or an intermediate structure.

Tissue sample holder 30 can include one or more handling portions configured to assist in the handling of tissue sample holder 30. For example, the handling portion(s) can facilitate the deployment and removal of tissue sample holder 30 to and from container 20 with embodiments in which tissue sample holder 30 is removably attached to container 20. The handling portions can include one or more knobs, dimples, nipples, surface textures and contours (e.g., convex protrusions and concave recessions), ribs, slots, grooves, arms, tabs, hooks, handles, and the like, spanning across and/or extending from various portions of sample tissue sample holder 30. These handling portions can comprise one or more materials that may improve a user's grip, such as various textured frictional coatings, or resilient materials, such as rubber or foam.

Referring to FIG. 5, tissue sample holder 30 can include one or more handling portion(s) comprising one or more arms 32 extending from a portion of base 31 (e.g., from its opposed ends) to facilitate the handling of tissue sample holder 30. Arms 32 can include a lower portion 32a attached to base 31, and an upper portion 32b that is attached to and extends from a portion of lower portion 32a (e.g., a distal end). Portions 32a, 32b can extend in a number of directions and/or at various angles with respect to each other and/or base 31 (and/or with respect to a portion of container 22 (e.g., base 22) when tissue sample holder 30 is attached thereto). Lower portion 32a can extend upwardly (e.g. orthogonally) with respect to upper surface 31a of base 31. Upper portion 32b preferably extends outwardly from lower portion 32a, to further facilitate handling of tissue sample holder 30. In some embodiments, lower portion 32a and upper portion 32b are of a sufficient length and configuration with respect to base 31 and container 20, such that tissue sample holder 30 can be deployed and/or removed from container 20 without draining the fluid from container 20, and without submersing upper portion 32b into the fluid. Such an embodiment can allow a user to attach and detach tissue sample 30 to and from container 20 without contaminating or contacting the fluid within container 20.

Tissue sample holder 30 can be attached to container 20 with sufficient strength and dimensional accuracy to support and align tissue sample holder 30 with respect to microtome 50, thus providing accurate and reliable sectioning of the portion(s) of sample(s) 70 with microtome 50 described herein. A strong and accurate alignment between tissue sample holder 30 and container 20 can also improve the alignment between tissue sample holder 30 and outlet(s) 40. Such alignment can improve the accuracy and reliability of the movement of the portion(s) of sample(s) 70 into outlet(s) 40 when they are sectioned by microtome 50.

Tissue sample holder 30 and container 20 can be attached, and preferably, removably attached, to each other with one or more engagement elements. The engagement elements described herein can comprise any of a variety of engagement and attachment structures and methods, including adhesive, snaps, hooks, tabs, buttons, a press fit, interference fit, snap fit, slots, grooves, screws, rivets, and the like. The engagement elements can be attached to and positioned along any of a number of portions of tissue sample holder 30 and container 20, such as base 31 (e.g., bottom surface 31b), arms 32, and/or base 22. In the illustrated embodiment, tissue sample holder 30 can include one or more tabs 33, extending from a portion of one or more arms 32. Tabs 33 can be configured to removably engage with a corresponding structure, such as a recess, slot or groove, within container 20 (e.g., on base 22 of container 20).

In some embodiments, tissue sample 70 can be attached directly to a portion of tissue sample holder 30, such as base 31 (e.g., upper surface 31a). In other embodiments, tissue sample 70 can be attached to an optional intermediary structure positioned between tissue sample 70 and tissue sample holder 30. Tissue sample 70 can be attached to tissue sample holder 30 or an intermediary structure using sutures, stitching, tissue adhesive (e.g., cyanoacrylate, etc.) or any suitable methods or structures known or described herein for attaching tissue samples to a plastic or other material used for tissue sample holder 30 or an intermediary structure.

It may be a challenge to mount and/or remove tissue sample(s) 70 onto tissue sample holder 30, as the available space between a tissue sample 70 mounted on base 31 and another, adjacent portion of tissue sample holder 30 (e.g., arms 32) may be limited, making the mounting and removal procedure difficult, even with forceps. The available space between two adjacent tissue samples 70 can also be limited, causing mounting and removal challenges in embodiments of apparatus 10 that employ two or more tissue samples 70 on tissue sample holder 30. The limited footprint on tissue sample holder 30 can be further exacerbated as the number of tissue samples 70 mounted on tissue sample holder 30 are increased for a given size blade 51 (FIG. 4), to increase the throughput of apparatus 10.

With continued reference to FIG. 5, to reduce the likelihood of the aforementioned difficulties in mounting and/or removing tissue sample(s) 70 to and from tissue sample holder 30, some embodiments of apparatus 10 can include one or more optional intermediary structures, such as removable plug(s) 80 that are removable from tissue sample holder 30 (e.g., from base 31). Plug(s) 80 can comprise similar or different material as tissue sample holder 30. In some embodiments, plug(s) 80 can comprise a material with different adherence and/or structural properties than tissue sample holder 30.

Plug(s) 80 can facilitate deployment and removal of a tissue sample 70 to and from tissue sample holder 30. For example, tissue sample(s) 70 can be removed from and/or mounted to plug(s) 80 while plug(s) 80 are detached and separated from tissue sample holder 30, to provide additional space during the removal/mounting procedure. Plug(s) 80 can also facilitate deployment and removal of tissue sample(s) 70 to and from tissue sample holder 30 without removing tissue sample holder 30 from container 20.

Plug 80 can comprise any of a number of shapes, such as those cross-sectional shapes described generally herein for tissue sample holder 30, or other shapes. In some embodiments, plug 80 is sized and shaped to support a single tissue sample 70, but it will be understood that plug 80 can be sized and shaped to support two or more tissue samples 70.

Referring to FIG. 5, plug(s) 80 can attach to tissue sample holder 30 using any of a number of engagement mechanisms, such as those described herein for attaching tissue sample holder 30 to container 20, or other mechanisms. In the illustrative embodiment, plug 80 includes a body 81 configured to engage with (e.g., slide, or insert into) a corresponding structure (e.g., a slot 34) on tissue sample holder 30. Body 81 can include one or more portions extending along and from various portions of its sides or surfaces, to provide additional engagement with tissue sample holder 30 and/or to provide an additional surface area on which a tissue sample 70 can be mounted. For example, body 81 can include an upper flange 82 extending from an upper portion of the sides of body 81, to provide additional surface area for mounting a tissue sample 70, and to provide further engagement with base 31 (e.g., upper surface 31a). For example, body 81 can include a lower flange 83 extending from a lower portion of the sides of body 81 to provide further engagement with a corresponding slot or other structure on base 31.

Plug(s) 80 can include one or more handling portions configured to assist in the handling of plug(s) 80, including any of those described herein for handling tissue sample holder 30, or other alternatives. In the illustrated embodiment, plug(s) 80 include a handle or tab 84 extending from a portion (e.g., an upper, lower or intermediary portion) of body 81.

Container 20 can comprise any of a number of shapes and materials capable of receiving and containing a fluid, preferably a liquid. For example, container 20 can comprise any of a number of different cross-sectional shapes, such as an approximately rectangular, elliptical, trapezoidal, or any other regular or irregular shape that forms a hollowed, inner volume when extended longitudinally, to hold fluid. Container 20 can comprise one or more sidewalls 21 extending from a base 22 of container 20, to form an internal volume within container 20. The positioning of base 22 is not limited to a lowermost extremity of container 20; base 22 can be positioned anywhere within an inner perimeter of sidewall(s) 21 to form an internal volume within container 20. An upper portion of container 20 can be closed, e.g., with a cover or lid. Preferably, a portion of container 20 (e.g., an upper or side portion) is open, or is configured with one or more openings, to facilitate insertion and removal of the tissue sample holder 30 to and from container 20, and to allow a portion of microtome 50 to section a portion 71 of tissue sample 70 supported on or within container 20.

Container 20 can comprise any of the materials described herein for tissue sample holder 30, and can comprise a similar or different material. Container 20 preferably comprises a hydrophobic (e.g., waterproof) material, such that container 20 can hold a liquid, and more preferably, a material suitable for use within a clinical environment for handling tissue samples. In one embodiment, container 20 comprises polycarbonate or a similar plastic. Container 20 can comprise an opaque, translucent, or transparent material. It will be understood that container 20 can comprise any combination of, and/or can be coated with, one or more of the aforementioned materials.

Apparatus 10 can include one or more inlets 43 configured to control (e.g., restrict and/or allow) fluid flow from a fluid source into container 20. Inlet 43 can be separately or integrally formed with respect to container 20. Inlet 43 can be attached to container 20 or an intervening structure, or can be the top opening of container 20, such that fluid can pour or flow from a position separate from container 20 (e.g., above container 20) and into container 20. Inlet 43 can comprise an opening extending through a portion of container 20, such as one or more of sidewalls 21 and/or base 22. In some embodiments, inlet 43 can include, or can be in communication with, one or more of a fitting, spout, nozzle, conduit, valve, flow controller, pump, pressure regulator or similar fluid control device configured to control the delivery of fluid into container 20. In FIG. 4, the fluid connection to inlet 43 is not shown for clarity. It will be understood that any such fluid control devices known or described herein can be manually or automatically controlled.

Apparatus 10 can include one or more drains configured to control (e.g., restrict and/or allow) fluid flow from container 20. Referring to FIGS. 4 and 5, apparatus 10 can include a level control drain 27 configured to maintain a level of fluid within container 20, such as a fluid level with respect to tissue sample 70 in container 20. In some embodiments, level control drain 27 can be configured such that fluid can flow across substantially the entirety of the height of tissue sample 70 when tissue sample 70 is in container 20 and throughout the sectioning of tissue sample 70 by microtome 50. In some embodiments, level control drain 27 can be configured such that the entirety of tissue sample 70 is immersed in fluid, to reduce damage or contamination to a portion 71 of tissue sample 70 sectioned by microtome 70. In some embodiments, drain 27 can be configured to provide a given level of fluid in container 20 that is a desired height above a tissue sample 70 mounted on tissue sample holder 30 in container 20. In some embodiments, the height or position of drain 27 can be adjustable with respect to a portion of container 20, tissue sample holder 30, tissue sample 70, and/or outlet(s) 40. Level control drain 27 can be separately or integrally formed with respect to container 20. Drain 27 can include, or can be in communication with, any of the fluid control devices known or described herein, configured to control the drain of fluid from container 20. In some embodiments, drain 27 can be a gravity drain. The connection of the drain 27 to a fluid sink is omitted from FIG. 4 for clarity.

Referring to FIG. 5, in some embodiments, drain 27 can comprise a drain opening or outlet 27a extending through a portion of container 20 (e.g., any of sidewall(s) 21 and/or base 22), to facilitate fluid flow from container 20. In some embodiments, drain 27 can comprise a drain inlet or opening 27b in fluid communication with drain outlet 27a. Drain outlet opening 27a and inlet opening 27b can be in fluid communication with each other through a number of different structures extending between outlet 27a and inlet 27b, such as a tube, conduit, etc. In the illustrated embodiment, drain 27 can include a drain body 27c with a channel extending therethrough that fluidly connects outlet 27a and inlet 27b.

Drain inlet 27b can be positioned at a given height with respect to base 22 of container 20, to maintain the aforementioned level of fluid within container 20. For example, drain inlet 27b can be positioned at a height sufficiently above the upper portion 71 of tissue sample 70, when tissue sample holder 30 is mounted within container 20, such that fluid can flow across substantially the entirety of the height of tissue sample 70 throughout the sectioning of tissue sample 70 by microtome 50. In some embodiments, inlet 27b can be positioned such that the cross-section of its opening is approximately parallel with the surface of a fluid held within container 20, to maintain a consistent fluid height within container 20 as the flow of fluid within container 20 varies. In the illustrative embodiment, inlet opening 27b extends through an upwardly-facing surface of drain body 27c, which is positioned with respect to container 20 to be approximately parallel with a fluid held within container 20.

The one or more inlet(s) 43, drain(s) 27, and/or outlet(s) 40 can be configured in any of a number of ways to facilitate movement of a sectioned portion 71 of tissue sample 70 into outlet 40 after being sectioned by microtome 50. For example, the flow rate of fluid through inlet(s) 43 can be adjusted to comprise a smooth, laminar flow of fluid within container 20 towards outlet 40, without causing turbulence that might cause the sectioned portion 71 of tissue sample 70 to move away from outlet 40. In some embodiments, inlet(s) 43 can include and/or be in fluid communication with a fluid control device that can be used to adjust such flow rate. In some embodiments, a valve can be in communication with inlet 43, to control the flow of fluid into container 20; in such embodiments, said valve can be closed during or subsequent to the sectioning of a portion 71 of tissue sample 70, to reduce fluid movement within container 20 and increase the likelihood of the sectioned portion 71 of tissue sample 70 to move into outlet 40 after the cutting stroke of microtome 50 is completed. In these embodiments, there will be no fluid entering the container 20 during the sectioning process, but fluid will be flowing out of outlets 40 as described above. The fluid level will drop during this time, but enough fluid can be present in the container to maintain everything appropriately submerged. After the sections exit the container 20 through outlets 40, the inlet can be turned back on, and the container fluid is replenished for the next cycle.

As described above, the flowpath of fluid within container 20 with respect to outlet(s) 40 and/or tissue sample(s) 70 facilitates the movement of a sectioned portion 71 of tissue sample 70 towards and into outlet 40. For example, inlet(s) 43 can be aligned with or can point towards tissue samples 70 and outlet 40, to direct fluid flow over tissue samples 70 and towards outlet 40. In some embodiments, inlet 43 and/or a portion of container 20 can include a channel 45 with a curvilinear path that facilitates a smooth flow of fluid within container 20, and reduces the likelihood of turbulence. In some embodiments, inlet 43 can be positioned within container 20 and with respect to drain 27, such that outlet(s) 40 and/or tissue sample holder 30 are positioned between inlet 43 and drain 27. Such embodiments can provide a flowpath between inlet 43 and drain 27 that allows fluid to flow over tissue samples 70 on tissue sample holder 30, and facilitates the flow of sectioned portions of tissue samples 70 towards outlet(s) 40. For example, inlet 43 can extend through a first portion (e.g., end) of a sidewall 21, with drain 27 extending through a second portion (e.g., an opposed end) of the sidewall 21, with tissue outlet(s) 40 extending through an intermediary portion of the sidewall 21.

In some embodiments, apparatus 10 can include an overflow drain 26 configured to maintain a level of fluid within container 20, for example, to prevent overflow of fluid from container 20. Overflow drain 26 can be substantially similar to the aforementioned embodiments of level control drain 27. Preferably, overflow drain 26 can be configured with an inlet 26a that is positioned with respect to container 20 and a fluid held within container 20, to maintain a level of the fluid within container 20 that is greater than the level of fluid maintained by level control drain 27. As such, inlet 26a can be a greater height than inlet 27b of level control drain 27 with respect to a fluid surface within container 20. Such an embodiment will prevent overflow of fluid from container 20 (e.g., over the upper edges of sidewall(s) 21) in the event of failure of drain 27 and/or in the event that the net flow of fluid into container 20 (e.g., from inlet 43 or other inlets) otherwise exceeds the flow of fluid from container 20 (e.g. from drain 27 and/or other drains or outlets, such as outlets 40).

Continuing to refer to FIGS. 4-6, outlet(s) 40 can be configured to allow flow of a fluid from the container 20, wherein the flow of fluid through the outlet(s) 40 causes a portion of the tissue sample sectioned by a microtome to move into the outlet(s) 40. Such movement can be facilitated through a pipette, a gravity drain, a siphon, or a pump or similar fluid control device in communication with outlet(s) 40. In embodiments with two or more outlet(s) 40, a flow through a first outlet 40 can cause a portion of a first tissue sample 70 to flow into the first outlet 40, and a flow through a second outlet 40 can cause a portion of a second tissue sample 70 to flow into the second outlet 40. It will be understood that apparatus 10 can include any of a number of different outlet(s) 40, and is shown with four outlets 40 for illustrative purposes only. Additionally, outlets 40 are shown to be approximately co-linear and co-planar, in a single row, although some embodiments can include a plurality of non-linear or non-planar outlets, and/or can form one or more rows and/or columns of outlets. Advantageously, the number and orientation of the outlets 40 is related to the number and orientation of the tissue samples 70, as described further herein.

Outlet 40 can be separately or integrally formed with respect to container 20. Outlet 40 can comprise an opening extending through a portion of container 20, such as base 22, a top or cover on container 20, or preferably, through a portion of sidewall 21, to allow a portion 71 of tissue sample 70 to flow from container 20. Thus, outlet 40 can be configured such that a sectioned portion of a tissue sample 70 can flow vertically (e.g., upwardly or downwardly), or preferably, horizontally from container 20, or other angles with respect to container 20.

In some embodiments, the shape and/or size of outlet 40 can be configured to facilitate the movement of a portion of a tissue sample 70 into outlet 40. The cross-sectional shape of outlet 40 can be any of a number of different shapes, such as a substantially elliptical, circular, rectangular, square, arc-shaped, round, non-round, or other regular or irregular shape. Outlet 40 can be a similar or different cross-sectional shape than tissue sample 70 and/or a sectioned portion 71 of tissue sample 70. In a preferred embodiment, outlet 40 can comprise a cross-sectional shape that is roughly similar to the side cross-sectional shape of an un-sectioned tissue sample 70 (e.g., an elongated shape, such as a rectangular or elliptical cross-section). Such similarity in shape can facilitate movement of any portion 71 of tissue sample 70 towards outlet 40, regardless of which portion (e.g., an upper, lower, or intermediary portion) of tissue sample 70 is being sectioned. One or more dimensions of outlet 40 (e.g., height, width, diameter) can be sized to be equal to or slightly larger than a sectioned portion 71 of tissue sample 70, to avoid snagging or interference when such sectioned portion moves into outlet 40.

In some embodiments, outlet 40 can include, or can be in communication with, one or more fittings, spouts, nozzles, conduits, valves, pumps, sensors, flow controllers, pressure regulators or similar fluid flow devices configured to control the flow of fluid through outlet 40 and the movement of sectioned portions of tissue samples towards outlet 40. In some embodiments, the amount of fluid flowed through outlet(s) 40 can be controlled to one or more flow rates, to facilitate such movement. As described above, and referring also to FIG. 2, in some embodiments, the amount of fluid flowing through outlet(s) 40 can be controlled to a first flow rate (e.g., a lower flow rate, or bleed) prior to completed sectioning of a portion 71 of tissue sample 70 (e.g., before or during the sectioning of tissue sample 70, but prior to completing a cutting stroke of a section of tissue sample 70 by microtome 50), and a second (e.g., greater) flow rate after completed sectioning of a portion 71 of tissue sample 70 (e.g., subsequent to completing a cutting stroke of microtome 50). Controlling the fluid flowing through outlet 40 to a first lower flow rate prior to completing the cutting stroke can help draw a portion 71 of tissue sample 70 towards outlet 40 during the sectioning cut, without causing the portion 71 to curl, roll, or flap over onto itself, reducing the accuracy of the cut. Controlling the fluid flowing through outlet 40 to a first lower flow rate can also reduce the amount of time that the second, increased flow rate need be applied to facilitate movement of the sectioned tissue sample 70 to outlet 40, reducing fluid consumption of apparatus 10

Referring to FIGS. 4 and 6, apparatus 10 can include one or more conduit(s) 41, 42 in fluid communication with one or more outlet(s) 40, to control the flow of fluid from container 20 through outlet(s) 40. For example, conduit 42 can be configured to provide the first lesser bleed flow rate through outlet 40, and conduit 41 can be configured to provide the second, greater flow rate. Conduit 41 can facilitate flow from outlet 40 to storage plate 90.

Conduits 41, 42 can comprise any of the cross-sectional shapes and/or sizes described herein for outlets 40, and can comprise a similar or different shape and/or size. In some embodiments, conduits 41 and/or 42 can be tapered in size and/or shape along their longitudinal length. For example, one or more dimensions (e.g., height, width, and/or diameter) of the interior cross-section of conduit section 41 can decrease in a longitudinal direction with respect to outlet 40, to facilitate movement of the sectioned portion 71 of tissue sample 70 from the outlet 40 through conduit 41. In a preferred embodiment, the interior cross-sectional shape of conduit 41 is tapered from an approximately elliptical cross-sectional shape at its interface with outlet 40 to an approximately circular cross-sectional shape downstream from outlet 40. In another preferred embodiment, conduit 41 comprises an inner diameter of approximately 0.25 in.

Conduits 41, 42 can comprise any of a variety of rigid, semi-rigid, or flexible hoses, channels, manifolds, or other structures, comprising any of a variety of materials, known or described herein suitable for channeling fluid. It will be understood that conduits 41, 42 need not include a completely enclosed lumen, and may comprise a partially open channel or similar configuration suitable for channeling fluid. It will also be understood that conduits 41 and 42 are optional, and that apparatus 10 can be configured such that fluid and a sectioned portion 71 of tissue sample 70 can flow (e.g., "pour,") directly from outlet(s) 40.

Conduit 41 can comprise one or more optional conduit sections. For example, conduit 41 can comprise a section 41a extending from opening 40 and through a portion of sidewall 21. However, it will be understood that section 41a can extend from another portion of container 20, and need not extend through sidewall 20 or be integrally formed therewith. In embodiments with two or more openings 40, two or more sections 41a can be configured to extend or separate outwardly (e.g., laterally) with respect to each other along their longitudinal length, to provide increased spacing between the downstream ends of adjacent sections 41a with respect to the upstream ends (e.g., at the interface of conduit(s) 41 with outlet(s) 40) (FIG. 4).

Apparatus 10 can include an optional manifold 130 through which a portion of conduit 41 (e.g., a section 41b) can extend. Section 41b can be integrally or separately formed with respect to manifold 130. Section 41b can be connected to and in fluid communication with conduit section 41a. Manifold 130 can include one or more fittings 131 connected to a manifold body 132, configured to connect and fluidly communicate with opening(s) 40, inlet 43, and/or drain 27. Fittings 131 can be a push-connect, barb, compression style, or other type of fluid connector. In some embodiments, manifold 130 can comprise a quick-connect, luer connection, or other removable connection 133 that facilitates the removal and reattachment of manifold 130 to opening(s) 40, inlet 43, and/or drain 27.

Conduit 41 can comprise a channel or conduit section 41c connected to and in fluid communication with section 41b. Conduit section 41c can be connected to section 41b, for example, with fitting 131. Section 41c can provide movement of fluid and a sectioned portion 71 of tissue sample 70 from outlet 40 to another device, such as storage plates 90.

Apparatus 10 can include one or more valves 120 in fluid communication with one or more outlet(s) 40, and configured to control the flow of fluid from the outlet 40. Valve 120 can be in communication with and mounted directly to outlet 40 (e.g., a portion of sidewall 21), or on an intermediary structure in communication with outlet 40, such as manifold 130 and/or a section of conduit 41. Valve 120 can comprise any of a number of different types of valves, such as a ball valve, gate valve, pinch valve, spool valve, diaphragm valve, butterfly valve, etc. Valve 120 can be actuated manually, hydraulically, electrically (e.g., a solenoid valve), and/or pneumatically. Preferably, valve 120 can comprise a valve with a configuration and/or materials suitable for use in a clinical environment, to reduce the likelihood of contamination of sectioned portions of tissue sample(s) 70.

Valve 120 can comprise a bleed, or non-fully closed valve that allows a greater flow in its open position, and a lesser flow in its closed position, or can be a shutoff valve that restricts any significant flow in a closed position. In one embodiment, valve 120 can comprise a pinch valve configured to control (e.g., restrict or allow) flow through a portion of conduit 41. In the illustrated embodiment, valve 120 controls flow from conduit section 41c and through an outlet conduit section 41d downstream of valve 120. Valve 120 can control flow from outlet 40 by clamping (e.g. pinching) and unclamping conduit 41 between an actuator, cylinder, or other clamping means 121 and a mandrel or other clamping means 122. Using a pinch valve configuration can clamp or pinch conduit 41 between an open and closed position, to allow and restrict flow, respectively, with reduced likelihood of contact between the internal components of valve 120 and the fluid or sectioned portions 71 of tissue sample 70 flowing through valve 120. As used herein, the "closed" position of a valve can allow a bleed or a lesser flow therethrough, for example, when valve 120 comprises a non-fully closed valve. A pinch valve can reduce the likelihood of contamination or damage to the sectioned portions 71 of tissue sample 70.

Valve 120 can be closed to provide a lower flow rate through outlet 40 prior to completing the cutting stroke during the sectioning of the portion 71 of tissue sample 70. When valve 120 is closed, the lower flow rate through outlet 40 can be approximately zero (for example, if valve 120 is a shutoff valve), or can comprise a flow greater than zero through outlet 40 (for example, if valve 120 is a non-fully closing or bleed valve, or in embodiments that allow flow through optional conduit 42, described further herein). Valve 120 can be opened to provide an increased flow rate subsequent to sectioning a portion 71 of tissue sample 70, to allow an increased fluid flow towards outlet 40, moving the sectioned portion of the tissue sample towards and into outlet 40. The amount of flow through outlet 40 when valve 120 is opened can be varied; in a preferred embodiment, the flow through outlet 40 when valve 120 is opened is approximately 500 mL/min.

Optional conduit 42 can be included with apparatus 10 to facilitate movement of a sectioned portion 71 of tissue sample 70 into outlet 40. Conduit 42 can be configured to flow an amount of fluid through outlet 40 that is advantageously less than the amount of fluid flowed through outlet 40 by conduit 41. For example, conduit 42 can be configured to provide the aforementioned lower flow rate, or bleed, through outlet 40 prior to completing the cutting stroke during the sectioning of the portion 71 of tissue sample 70. Conduit 42 can provide lesser fluid flow through outlet 40, for example, by sizing the inner channel of conduit 42 to be a smaller cross-sectional area than that of conduit 41. Additionally or alternatively, conduit 41 and/or 42 can include any fluid control devices known or described herein that are configured to provide different flow rates than the other of conduit 41 and 42, or flow devices in fluid communication therewith. For example, an optional flow controller or needle valve 45 can be in communication with conduit 42 to control the flow therethrough. In an embodiment, needle valve 45 and/or conduit 42 can be configured to allow a bleed flow rate of approximately 25 ml/min.

It will be understood that the lower flow provided by conduit 42 can be implemented as an alternative or in combination with a lower flow (e.g., bleed) provided with conduit 41 (e.g., when valve 120 comprises a bleed valve). It will also be understood that the bleed through conduit 42 can be continuous (e.g., used when conduit 41 provides a higher flow rate), or can be switched sequentially with respect to a higher flow rate through conduit 41 (e.g., when valve 120 is opened).

In the illustrated embodiment, conduit 42 can be in fluid communication with outlet 40 at a connection point 44 located in first conduit 41. Connection point 44 can comprise any of a number of structures, such as a tee-fitting, y-fitting, manifold, banjo fitting, and the like. In some embodiments, connection point 44 can comprise a valve that controls (e.g., restricts or allows) fluid communication between outlet 40 (e.g., portion 41c of conduit 41), and either or both of conduit 42 and conduit section 41(d). The fluid control devices known or described herein can be positioned to control flow in conduits 41 and/or 42 upstream and/or downstream of connection point 44. In some embodiments, a filter can be positioned within conduit 41 and/or 42 to allow the flow of fluid into conduit 42, but prevent the likelihood of a sectioned portion 71 of tissue sample 70 flowing into conduit 42.

Figure 7:
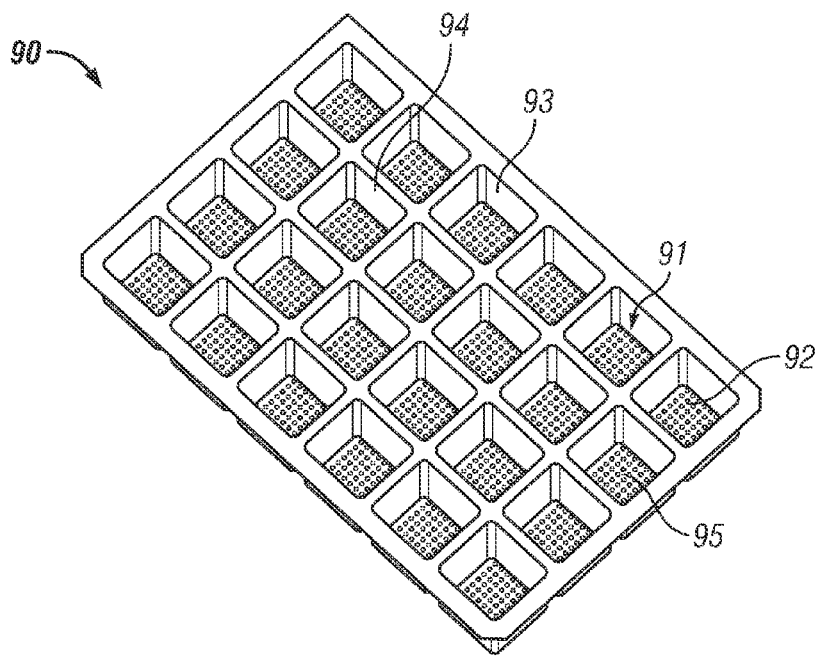
FIG. 7 is a perspective view of one embodiment of a storage plate configured to receive one or more portions of a tissue sample.

Referring to FIGS. 4 and 7, the storage plate 90 can be configured to include one or more wells 91 configured to receive one or more sectioned portion(s) of tissue sample(s) 70. For example, after a portion 71 of tissue sample 70 is sectioned by microtome 50, it can flow through outlet 40, and from outlet 40 into well 91. In some embodiments, the portion 71 of tissue sample 70 flows into well 91 from an end of conduit 41, such as section 41c. Storage plate 90 and/or well(s) 91 can comprise any of the shapes and/or materials described generally herein for container 20.

Storage plate 90 and well(s) 91 can comprise any of a number of suitable configurations to receive a sectioned tissue sample. In the illustrated embodiment, storage plate 90 comprises one or more sidewalls 93 extending from a base 95 to form an interior volume configured to receive one or more sectioned tissue samples 70. Preferably, storage plate 90 comprises one or more inner dividing walls 94 to form a plurality of wells 91. One or more apertures 92 can extend through a portion of base 95, to allow fluid to flow through a portion of the well without allowing a tissue sample section to flow through the aperture(s) 92. Apertures 92 can also increase the storage density of the sectioned portions of tissue samples 70 that can be stored in wells 91, by reducing the amount of fluid within wells 91 and allowing the sectioned portions to stack, contact each other, and/or otherwise be stored in a more efficient, compact manner. It will be understood that the number of wells 91 in each storage plate 90 (e.g., the illustrated quantity of 24, in a 4×6 matrix), and/or the number of apertures 92 in each well 91 can be any of a number of quantities, and the quantities shown in FIGS. 4 and 7 are for illustrative purposes only.

Figure 8:
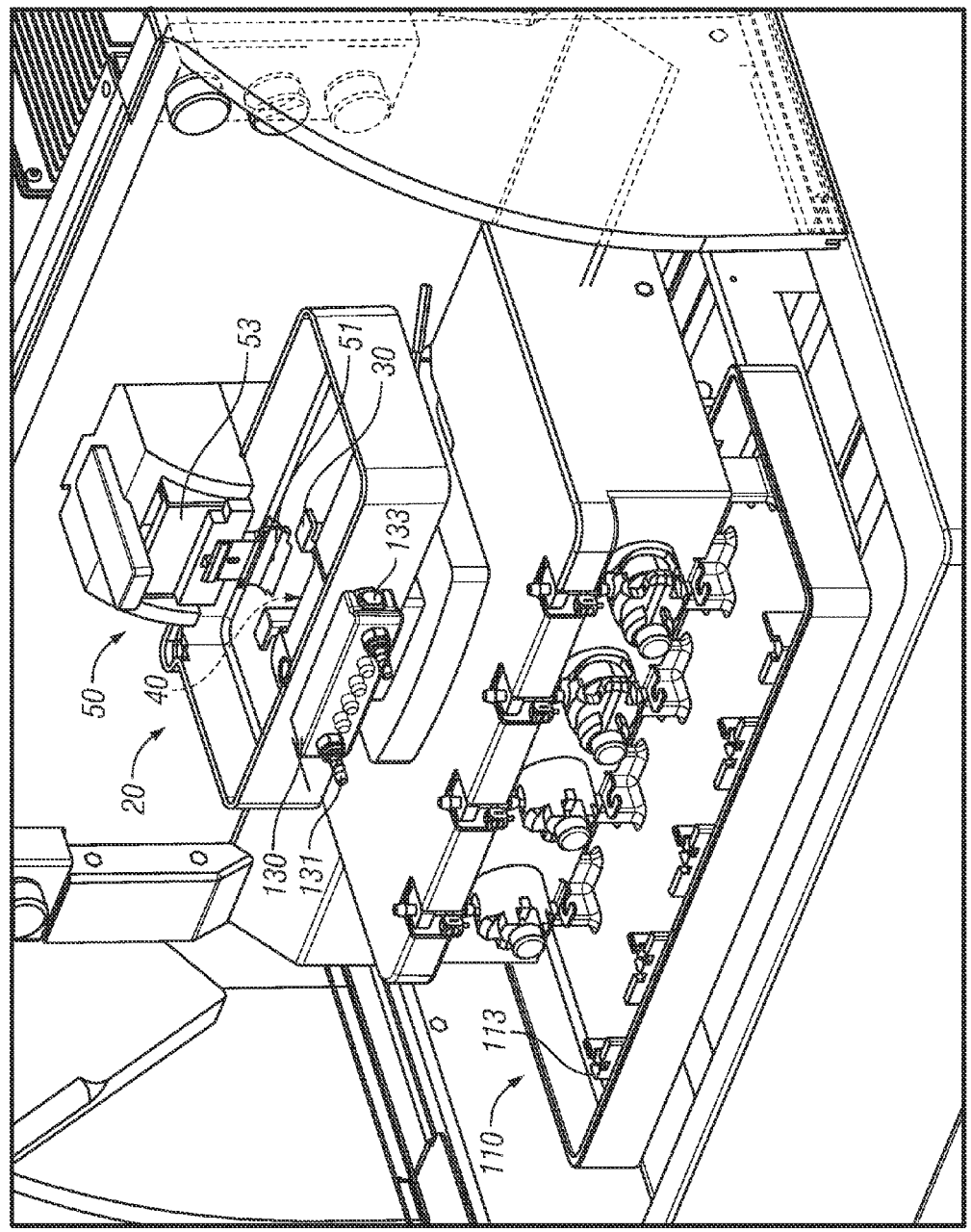
FIG. 8 is a perspective view of one embodiment of the apparatus for handling a portion of a tissue sample of FIG. 4, with some components not shown for clarity.

Referring to FIGS. 4, 7 and 8, apparatus 10 can include tray 110 configured to support the one or more storage plates 90. Tray 110 can comprise any of the shapes and/or materials described herein generally for container 20. Tray 110 can comprise a base 112 with one or more sidewalls 111 configured to form an interior volume in which storage plate(s) 90 can be contained and supported. Tray 110 can include one or more optional supporting members 113 (e.g., brackets) attached, e.g., to sidewall(s) 111 and/or base 112, to provide additional support to the one or more storage plate(s) 90. Such additional support can improve the accuracy of the transfer of sectioned tissue samples into storage plate(s) 90. Tray 110 can be sized to allow storage plate(s) 90 to remain submerged under fluid, to protect tissue sample sections stored within storage plate(s) 90. Tray 110 can comprise one or more drains to control the flow of fluid from tray 110, similar to drains 26, 27 of container 20 (FIGS. 4-5), and to manage the flow of fluid through aperture 92 in storage plate 90, and into tray 110.

Tray 110 can be moveable with respect to one or more other portions of apparatus 10, such as microtome 50, container 20, outlet(s) 40, and/or conduit(s) 41 (e.g., the conduit outlet of section 41(d)). Such movement can allow tray 110 (and thus storage plates 90) to be indexed with respect to outlet(s) 40. This indexing can allow a first sectioned portion of a tissue sample 70 to be flowed from outlet 40 into a first well 91 on a storage plate 90, after which storage plate 90 can be moved (e.g., in one or more of directions 501, 502, 505, 506), such that storage plate 90 can subsequently receive a second sectioned portion of a tissue sample 70 from outlet 40 into first well 91 or a second well 91. The relative movement between tray 110 and another portion of apparatus 10 can be provided manually or automatically through any of a number of movable elements, such as those known or described herein for providing relative movement between microtome 50 and tissue sample(s) 70.

In some embodiments, apparatus 10 can include one or more optional sensors (e.g., pressure, temperature, proximity, location (e.g., an encoder), flow, fluid level sensors, etc.) to provide feedback, and/or to allow for open or closed loop control, or manual adjustment, of various aspects of apparatus 10. For example, an optional sensor 46 (FIG. 6) can be employed proximate to or within outlet 40 and/or conduit 41, to detect when (and if) a sectioned tissue sample successfully passes through outlet 40 and/or conduit 41.

In some embodiments, apparatus 10 can include a temperature control system to control the temperature of (e.g., heat or cool) various components of apparatus 10, or materials being worked upon by apparatus 10. For example, it may be advantageous to control the temperature of the fluid flowing through or across one or more of container 20, tissue sample holder 30, outlet(s) 40, drain(s) 26, 27, conduits 41, 42, storage plate 90, tray 110, and/or other components described herein. Such temperature control can maintain the integrity of a tissue sample or section as it is supported, sectioned, moved, and/or stored by apparatus 10. Such a temperature control system can include one or more heating and/or cooling elements, and/or temperature sensors to control said heating and/or cooling elements in a closed or open-loop control configuration. In some embodiments, the temperature of the fluid in a reservoir that feeds the container is maintained at a desired low temperature. The fluid may be cycled through the system at a rate that significant temperature increase when the fluid is in the system is avoided and the only cooling element is associated with the reservoir rather than with any of the fluid handling components described in detail herein.

Referring again to FIGS. 2-4, in some embodiments, the method of handling can further comprise flowing a fluid from the one or more outlets 40 to storage plate 90, causing the one or more portions of the tissue sample 70 to move from the one or more outlets 40 into one or more wells 91 of the storage plate 90. In some embodiments, the method can further comprise repeatedly flowing a fluid from the at least one outlet 40 to storage plate 90, and indexing the storage plate 90 from a first position to a second position between steps of flowing a fluid from the one or more outlets 40 to the storage plate 90, causing a first portion 71 of the tissue sample 70 to move into a first well 91 during the first step, and a second portion of the tissue sample to move into a second well 91 during the second step. In some embodiments, flowing the fluid from the one or more outlets 40 to the storage plate 90 can comprise flowing the fluid from a plurality of outlets 40 to a plurality of storage plates 90.

The container 20, tissue sample holder 30, plug 80, storage plate 90, tray 110, and/or microtome 50 described herein may be attached together at the point of manufacture. Alternatively, any of these components or others described herein can be manufactured as an accessory or replacement part and sold independently. For example, container 20 can be sold without a tissue sample holder 30; tissue sample holder 30 can be sold without plug 80; tray 110 can be sold without storage plate 90, etc. Any combination of container 20, tissue sample holder 30, plug 80, storage plate 90, tray 110, and/or microtome 50 can also be supplied as a kit, for example, wherein the container 20, tissue sample holder 30, plug 80, storage plate 90, tray 110, and/or microtome 50 can be supplied separately and then assembled by the user.

Embodiments described herein provide less expensive, efficient apparatuses and processes for handling a portion of a tissue sample sectioned by a microtome that can provide increased quality, accurately sectioned tissue samples, with reduced waste and contamination. Some embodiments provide a level of repeatability and accuracy that can allow 120-140 portions of tissue samples to be sectioned from a single mouse brain. Some embodiments allow one or more sectioned portions of one or more tissue samples to remain immersed in fluid throughout one or more operations, and preferably, the entirety, of the sectioning, handling, and storage process, to prevent contamination or damage to the sectioned tissue samples. Some embodiments allow one or more portions of a tissue sample to be sectioned, handled, and/or stored, without requiring contact by laboratory personnel or external tools (e.g., forceps). Some embodiments allow one or more of the sectioning, handling and/or storage steps to be controlled automatically, reducing or eliminating manual input from laboratory personnel during these step(s). Some embodiments allow two or more portions of two or more tissue samples to be sectioned during the same cutting stroke of a microtome blade.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. An apparatus for handling a portion of a tissue sample, the apparatus comprising:
    a microtome for sectioning a portion of a tissue sample;
    a container containing a liquid;
    a tissue sample holder in the container, a blade of the microtome being disposed proximate the tissue sample holder for sectioning the portion of the tissue sample held by the tissue sample holder;
    an outlet from the container configured to allow flow of the liquid from the container;
    wherein the outlet is positioned proximate to the tissue sample holder such that flow of the liquid through the outlet causes the portion of the tissue sample sectioned by the microtome to move into the outlet; and
    a storage plate, the storage plate including one or more wells positioned, with respect to the outlet, to receive the portion of the tissue sample sectioned by the microtome from the outlet, wherein one or more of the one or more wells comprises one or more apertures to allow the liquid to flow through the one or more a apertures without allowing the portion of the tissue sample sectioned by the microtome to flow through the one or more apertures.

2. The apparatus of claim 1, wherein the microtome includes a control system configured to automate a portion of the microtome.

3. The apparatus of claim 1, wherein the tissue sample holder is removable from the container.

4. The apparatus of claim 1, wherein the tissue sample holder comprises at least two separable portions.

5. The apparatus of claim 1, the outlet comprising a first outlet and a second outlet positioned proximate to the tissue sample holder such that flow of the liquid through the first outlet causes a portion of a first tissue sample sectioned by the microtome to flow into the first outlet, and flow of the liquid through the second outlet causes a portion of a second tissue sample sectioned by the microtome to flow into the second outlet.

6. The apparatus of claim 1, comprising a drain positioned in the container.

7. The apparatus of claim 1, comprising a valve in fluid communication with the outlet and configured to control the flow of the liquid from the outlet.

8. The apparatus of claim 1, comprising a first conduit in fluid communication with the outlet.

9. The apparatus of claim 8, comprising a second conduit in fluid communication with the outlet.

10. The apparatus of claim 9, wherein the second conduit is in fluid communication with the outlet at a connection point located in the first conduit, and further comprising a valve configured to control the flow of the liquid fluid from the first conduit, the valve located downstream of the connection point.

11. The apparatus of claim 1, further comprising a moveable tray that holds configured to hold the storage plate with respect to the outlet.

12. The apparatus of claim 1, wherein the cross-section of at least one of the one or more outlets is round.

* * * * *

UNITED STATES PATENT AND TRADEMARK OFFICE
CERTIFICATE OF CORRECTION

PATENT NO. : 8,967,024 B2  
APPLICATION NO. : 13/187416  
DATED : March 3, 2015  
INVENTOR(S) : Sanjay Shivayogi Magavi et al.

Page 1 of 1

It is certified that error appears in the above-identified patent and that said Letters Patent is hereby corrected as shown below:

In the claims

In column 18 at line 26 (approx.), In Claim 1, after "more" delete "a".

In column 18 at line 57 (approx.), In Claim 10, after "liquid" delete "fluid".

In column 18 at line 61 (approx.), In Claim 11, after "holds" delete "configured to hold".

Signed and Sealed this  
Twenty-ninth Day of December, 2015

Michelle K. Lee  
*Director of the United States Patent and Trademark Office*